United States Patent
Inoue et al.

(10) Patent No.: US 11,017,453 B2
(45) Date of Patent: May 25, 2021

(54) GLASSES SELLING SYSTEM, LENS COMPANY TERMINAL, FRAME COMPANY TERMINAL, GLASSES SELLING METHOD, AND GLASSES SELLING PROGRAM

(71) Applicant: NIKON CORPORATION, Tokyo (JP)

(72) Inventors: Hideya Inoue, Yokohama (JP); Yasuteru Fukawa, Tokyo (JP); Koji Yamagaki, Yokosuka (JP)

(73) Assignee: NIKON CORPORATION, Tokyo (JP)

( * ) Notice: Subject to any disclaimer, the term of this patent is extended or adjusted under 35 U.S.C. 154(b) by 284 days.

(21) Appl. No.: 16/025,477

(22) Filed: Jul. 2, 2018

(65) Prior Publication Data

US 2018/0308153 A1    Oct. 25, 2018

Related U.S. Application Data

(60) Division of application No. 14/793,028, filed on Jul. 7, 2015, now Pat. No. 10,043,207, which is a division
(Continued)

(30) Foreign Application Priority Data

Mar. 16, 2010  (JP) ................................. 2010-059685

(51) Int. Cl.
   *G06Q 30/06*       (2012.01)
   *G16H 40/67*       (2018.01)
   (Continued)

(52) U.S. Cl.
   CPC .......... *G06Q 30/0633* (2013.01); *A61B 3/111* (2013.01); *G02C 7/027* (2013.01);
   (Continued)

(58) Field of Classification Search
   None
   See application file for complete search history.

(56) References Cited

U.S. PATENT DOCUMENTS

| 4,980,993 A | 1/1991 | Umezaki |
| 5,475,425 A | 12/1995 | Przyborski et al. |

(Continued)

FOREIGN PATENT DOCUMENTS

| CN | 1476574 | 2/2004 |
| CN | 101344971 | 1/2009 |

(Continued)

OTHER PUBLICATIONS

Tant, L., "Keep an Eye on Glasses as Accessories," The Vancouver Sun [Vancouver, B.C.], 3* Edition, Mar. 3, 1988: C2. (Year: 1988).*

(Continued)

*Primary Examiner* — Nicholas D Rosen

(57) ABSTRACT

A selling server stores prescription data of a customer transmitted from an optometrist terminal of an optometrist who performs optometry for a glasses prescription through a communication line in association with customer identification information, transmits image data of a frame candidate group of glasses to a customer terminal, transmits image data of a lens candidate group of the glasses to the customer terminal, receives information relating to a frame and a lens purchased by the customer and determined on the basis of a combined image of a frame image selected by the customer, a lens image selected by the customer, and a face image of the customer, and transmits prescription data of the customer to a lens company terminal of a lens company which processes the lens purchased by the customer.

14 Claims, 8 Drawing Sheets

Related U.S. Application Data of application No. 13/613,562, filed on Sep. 13, 2012, now abandoned, which is a continuation of application No. PCT/JP2011/056073, filed on Mar. 15, 2011.

(51) Int. Cl.

| | | |
|---|---|---|
| *A61B 3/11* | (2006.01) | |
| *G02C 13/00* | (2006.01) | |
| *G02C 7/02* | (2006.01) | |
| *G16H 20/40* | (2018.01) | |

(52) U.S. Cl.
CPC ......... *G02C 13/003* (2013.01); *G02C 13/005* (2013.01); *G06Q 30/0601* (2013.01); *G06Q 30/0641* (2013.01); *G06Q 30/0643* (2013.01); *G06Q 30/0603* (2013.01); *G06Q 30/0631* (2013.01); *G16H 20/40* (2018.01); *G16H 40/67* (2018.01)

(56) References Cited

U.S. PATENT DOCUMENTS

| | | | |
|---|---|---|---|
| 5,907,583 | A | 5/1999 | Sakoda et al. |
| 5,960,411 | A | 9/1999 | Hartman et al. |
| 5,983,201 | A | 11/1999 | Fay |
| 6,533,418 | B1 | 3/2003 | Izumitani et al. |
| 6,792,401 | B1 | 9/2004 | Nigro et al. |
| 7,062,454 | B1 | 6/2006 | Giannini et al. |
| 7,062,722 | B1 | 6/2006 | Carlin et al. |
| 7,188,082 | B2 | 3/2007 | Keane et al. |
| 7,222,091 | B2 | 5/2007 | Yoshida |
| 9,058,765 | B1 * | 6/2015 | Mallick ................. G06F 3/0482 |
| 10,043,207 | B2 * | 8/2018 | Inoue ..................... G02C 7/027 |
| 2001/0042028 | A1 | 11/2001 | Yoshida |
| 2001/0051953 | A1 | 12/2001 | Fukuma et al. |
| 2002/0176052 | A1 | 11/2002 | Ueno |
| 2004/0015412 | A1 | 1/2004 | Shinbo |
| 2004/0034564 | A1 | 2/2004 | Liu |
| 2004/0064376 | A1 | 4/2004 | Yoshida |
| 2004/0107117 | A1 | 6/2004 | Denny |
| 2004/0176977 | A1 | 9/2004 | Broderick et al. |
| 2005/0162419 | A1 | 7/2005 | Kim et al. |
| 2005/0175234 | A1 | 8/2005 | Sakamoto |
| 2005/0207617 | A1 | 9/2005 | Sarnoff |
| 2005/0240581 | A1 | 10/2005 | Smith et al. |
| 2006/0195362 | A1 | 8/2006 | Jacobi et al. |
| 2008/0009348 | A1 | 1/2008 | Zalewski et al. |
| 2008/0033836 | A1 | 2/2008 | Shinohara et al. |
| 2008/0043039 | A1 | 2/2008 | Yamaji et al. |
| 2008/0235047 | A1 | 9/2008 | Broderick et al. |
| 2009/0106033 | A1 | 4/2009 | Thangavelu et al. |
| 2009/0116126 | A1 | 5/2009 | Berzon et al. |
| 2009/0318112 | A1 | 12/2009 | Vasten |
| 2010/0114540 | A1 | 5/2010 | Shinohara et al. |

FOREIGN PATENT DOCUMENTS

| | | |
|---|---|---|
| EP | 1011006 | 6/2000 |
| EP | 1336924 A1 | 8/2003 |
| EP | 1501046 | 1/2005 |
| EP | 1833025 | 9/2007 |
| JP | 2001-350982 | 12/2001 |
| JP | 2002-010977 | 1/2002 |
| JP | 2002-162607 | 6/2002 |
| JP | 2004-094773 | 3/2004 |
| JP | 2004-118208 | 4/2004 |
| JP | 2004-287626 | 10/2004 |
| JP | 2006-185329 | 7/2006 |
| WO | WO-9729441 A1 | 8/1997 |
| WO | WO-9940526 A1 | 8/1999 |
| WO | WO 03/081536 A1 | 10/2003 |

OTHER PUBLICATIONS

Feagin, R.M., "Make Those Peepers Keepers," News Journal [Mansfield, Ohio] Jul. 7, 2003: C.1. (Year: 2003).*
Chinese Office Action dated Jul. 31, 2015 in corresponding Chinese Patent Application No. 201180013956.X.
Chinese Office Action dated Dec. 3, 2015 in corresponding Chinese Patent Application No. 201180013956.X.
Chinese Office Action dated Jul. 6, 2016 in corresponding Chinese Patent Application No. 201180013956.X.
Chinese Office Action dated May 9, 2017 in corresponding Chinese Patent Application No. 201180013956.X.
Chinese Reexamination Decision dated Oct. 31, 2017 in related Chinese Application No. 201180013956.X.
Indian Office Action dated Jun. 20, 2018 in related Indian Patent Application No. 8165/DELNP/2012.
Office Action dated Jul. 2, 2019 in related Chinese patent application No. 201610879718.1.
Chinese Office Action dated Feb. 2, 2019 in Chinese Application No. 201610879718.1.
Japanese Office Action dated Feb. 12, 2014 in corresponding Japanese Patent Application No. 2010-059685.
Chinese Office Action dated Feb. 2, 2015 in corresponding Chinese Patent Application No. 201180013956.X.
International Search Report dated Jun. 7, 2011, issued in corresponding PCT Patent Application No. PCT/JP2011/056073.
PCT Written Opinion of the International Searching Authority dated Jun. 7, 2011, issued in corresponding PCT Patent Application No. PCT/JP2011/056073.
Gottschalk, M., "Glasses, the Windows to Your Eyes Make a Spectacle with the Right Frame for You," San Jose Mercury News, Nov. 29, 1988, Morning Final Edition, p. 1G.
Constantine-Smith, N., "Would You Prescribe?", Optician, vol. 229, No. 6002, pp. 36-39, May 30, 2005.
Troy, M. "OTC Dept. Maintains Momentum," Drug Store News, vol. 19, No. 1, p. 25, Jan. 6, 1997.
U.S. Appl. No. 14/793,028, filed Jul. 7, 2015, Hideya Inoue et al., Nikon Corporation.
Office Action dated Jan. 3, 2013 in U.S. Appl. No. 13/613,562.
Office Action dated May 10, 2013 in U.S. Appl. No. 13/613,562.
Office Action dated Aug. 11, 2014 in U.S. Appl. No. 13/613,562.
Office Action dated Jan. 7, 2015 in U.S. Appl. No. 13/613,562.
Advisory Action dated Apr. 16, 2015 in U.S. Appl. No. 13/613,562.
Office Action dated Dec. 8, 2017 in U.S. Appl. No. 14/793,028.
Notice of Allowance dated Apr. 4, 2018 in U.S. Appl. No. 14/793,028.
Chinese Office Action dated Oct. 9, 2019 in corresponding Chinese Patent Application No. 201610879718.1.

\* cited by examiner

FIG. 2

| CUSTOMER IDENTIFICATION INFORMATION | MYOPIC POWER | HYPEROPIC POWER | ASTIGMATIC POWER | ASTIGMATIC AXIS ANGLE | INTER-PUPIL DISTANCE | ... |
|---|---|---|---|---|---|---|
| ... | ... | ... | ... | ... | ... | ... |
| ... | ... | ... | ... | ... | ... | ... |

GLASSES SELLING SYSTEM, LENS COMPANY TERMINAL, FRAME COMPANY TERMINAL, GLASSES SELLING METHOD, AND GLASSES SELLING PROGRAM

CROSS-REFERENCE TO RELATED APPLICATION

This is a Divisional Application of U.S. Ser. No. 14/793,028, filed Jul. 7, 2015 which is a Divisional Application of U.S. Ser. No. 13/613,562, filed Sep. 13, 2012 which is a Continuation Application of International Application No. PCT/JP2011/056073, filed Mar. 15, 2011, which claims priority to Japanese Patent Application No. 2010-059685 filed on Mar. 16, 2010. The contents of the aforementioned applications are incorporated herein by reference.

BACKGROUND

Field of the Invention

The present invention relates to a technique for selling glasses using network communication.

Description of Related Art

In general, when purchasing glasses, first, a purchaser visits a glasses shop, and visual acuity measurement or optometry, such as an inter-pupil distance, is performed in an ophthalmic office or the like which is established at the glasses shop. The purchaser selects a glasses frame based on the purchaser's preference from a plurality of glasses frames prepared at a glasses shop. The purchaser selects the type of lens, such as the material or the refractive index of the lens, in accordance with the optometry result. The glasses shop places an order for the selected lens with a lens company. The lens company manufactures and processes the lens on the basis of design data of the lens based on the optometry result, and distributes the processed lens to the glasses shop which places the order. The glasses shop processes the lens in conformity with the frame, and inserts the lens into the frame to assemble the glasses. The purchaser visits the glasses shop again and receives the assembled glasses.

According to the technique described in Japanese Unexamined Patent Application, First Publication No. 2002-162607, the purchaser of the glasses inputs the optometry result to a terminal on the basis of a prescription according to diagnosis of an ophthalmologist or a prescription, such as the inter-pupil distance or the like measured at an automated shop or the like. The terminal transmits the input optometry result to a server which is connected to the terminal through Internet. On the server side, information is transmitted and received between a plurality of servers, such as a frame supplier server and a lens supplier server, thereby distributing the processed glasses to the purchaser.

However, in the technique described in Japanese Unexamined Patent Application, First Publication No. 2002-162607, the purchaser of the glasses should input the optometry result to the terminal on the basis of a prescription according to diagnosis of the ophthalmologist or a prescription, such as the inter-pupil distance or the like measured at an automated shop or the like. The optometry result includes a plurality of pieces of technical information, and it is often difficult for a general purchaser to understand the meaning of each item of the prescription. For this reason, a case where it may be difficult for the purchaser to discriminate information required for purchasing the glasses and to input the information to the terminal is considered. A case where the purchaser reads information necessary for purchasing glasses from a prescription given by an ophthalmologist, an automated shop, or the like and inputs information to the terminal, sufficient information for glasses manufacturing and processing may not be transmitted to the server due to erroneous input of data or insufficient input of necessary information is also considered. Accordingly, a case where appropriate glasses may not be manufactured and processed, and the purchaser does not obtain sufficient visual acuity with the glasses purchased in this way or feels a sense of discomfort at the time of wearing is considered. Even when glasses are sold through a network, it is desirable to sell more appropriate glasses more simply to the purchaser in accordance with the optometry result of the purchaser.

A purpose of some aspects of the present invention is to provide a glasses selling system, a lens company terminal, a frame company terminal, a glasses selling method, and a glasses selling program capable of simply selling appropriate glasses for a purchaser when selling glasses using network communication.

SUMMARY

A first aspect of the invention provides a glasses selling system including a selling server which is connected to a customer terminal of a customer who purchases glasses through a communication line. The selling server is connected to an optometrist terminal of an optometrist who performs optometry for a glasses prescription through the communication line. The selling server includes a prescription data storage unit which stores prescription data of the customer transmitted from the optometrist terminal in association with customer identification information for identifying the customer, a frame image transmission unit which transmits image data of a frame candidate group of the glasses to the customer terminal, a lens image transmission unit which transmits image data of a lens candidate group of the glasses to the customer terminal, a purchase request receiving unit which receives information relating to a frame and a lens purchased by the customer and determined on the basis of a combined image of a frame image selected by the customer, a lens image selected by the customer, and a face image of the customer, and a prescription data transmission unit which transmits the prescription data of the customer to a lens company terminal of a lens company manufacturing the lens purchased by the customer.

A second aspect of the invention provides a lens company terminal which is connected to a selling server used in a glasses selling system for selling glasses to a customer through a communication line. The selling server is connected to an optometrist terminal of an optometrist who performs optometry for a glasses prescription through the communication line. The selling server includes a prescription data storage unit which stores prescription data of the customer transmitted from the optometrist terminal in association with customer identification information for identifying the customer, a purchase request receiving unit which receives information relating to a lens purchased by the customer determined on the basis of a combined image of a frame image selected by the customer, a lens image selected by the customer, and a face image of the customer, and a prescription data transmission unit which transmits the prescription data of the customer and information relating to the lens purchased by the customer to a lens company terminal. The lens company terminal includes a prescription data receiving unit which receives the prescription data of the customer and information relating to the lens purchased by the customer transmitted from the selling server.

A third aspect of the invention provides a frame company terminal which is connected to a selling server used in a glasses selling system for selling glasses to a customer through a communication line. The selling server is connected to an optometrist terminal of an optometrist who performs optometry for a glasses prescription through the communication line. The selling server includes a prescription data storage unit which stores prescription data of the customer transmitted from the optometrist terminal in association with customer identification information for identifying the customer, a purchase request receiving unit which receives information relating to a lens purchased by the customer determined on the basis of a combined image of a frame image selected by the customer, a lens image selected by the customer, and a face image of the customer, and a frame information transmission unit which transmits information relating to a frame purchased by the customer to a frame company terminal. The frame company terminal includes a frame information receiving unit which receives the information relating to the frame purchased by the customer transmitted from the selling server.

A fourth aspect of the invention provides a glasses selling method including a prescription data storage step of storing prescription data of a customer transmitted from an optometrist terminal of an optometrist who performs optometry for a glasses prescription in association with customer identification information for identifying the customer, a frame image transmission step of transmitting image data of a frame candidate group of glasses to a customer terminal of the customer, a lens image transmission step of transmitting image data of a lens candidate group of the glasses to the customer terminal, a purchase request receiving step of receiving information relating to a frame and a lens purchased by the customer and determined on the basis of a combined image of a frame image selected by the customer, a lens image selected by the customer, and a face image of the customer, and a prescription data transmission step of transmitting prescription data of the customer to a lens company terminal of a lens company manufacturing the lens purchased by the customer.

A fifth aspect of the invention provides a glasses selling program which causes a computer to execute a prescription data storage step of storing prescription data of a customer transmitted from an optometrist terminal of an optometrist who performs optometry for a glasses prescription in association with customer identification information for identifying the customer, a frame image transmission step of transmitting image data of a frame candidate group of glasses to a customer terminal of the customer, a lens image transmission step of transmitting image data of a lens candidate group of the glasses to the customer terminal, a purchase request receiving step of receiving information relating to a frame and a lens purchased by the customer and determined on the basis of a combined image of a frame image selected by the customer, a lens image selected by the customer, and a face image of the customer, and a prescription data transmission step of transmitting prescription data of the customer to a lens company terminal of a lens company manufacturing the lens purchased by the customer.

According to the aspects of the invention, it becomes possible to provide a glasses selling system, a lens company terminal, a frame company terminal, a glasses selling method, and a glasses selling program capable of simply selling appropriate glasses for a purchaser when selling glasses using network communication.

BRIEF DESCRIPTION OF THE DRAWINGS

FIG. 2 is a diagram showing a data example which is stored in a prescription data storage unit according to an embodiment of the invention.

DESCRIPTION OF EMBODIMENTS

Hereinafter, an embodiment of the invention will be described with reference to the drawings.

Figure 1:
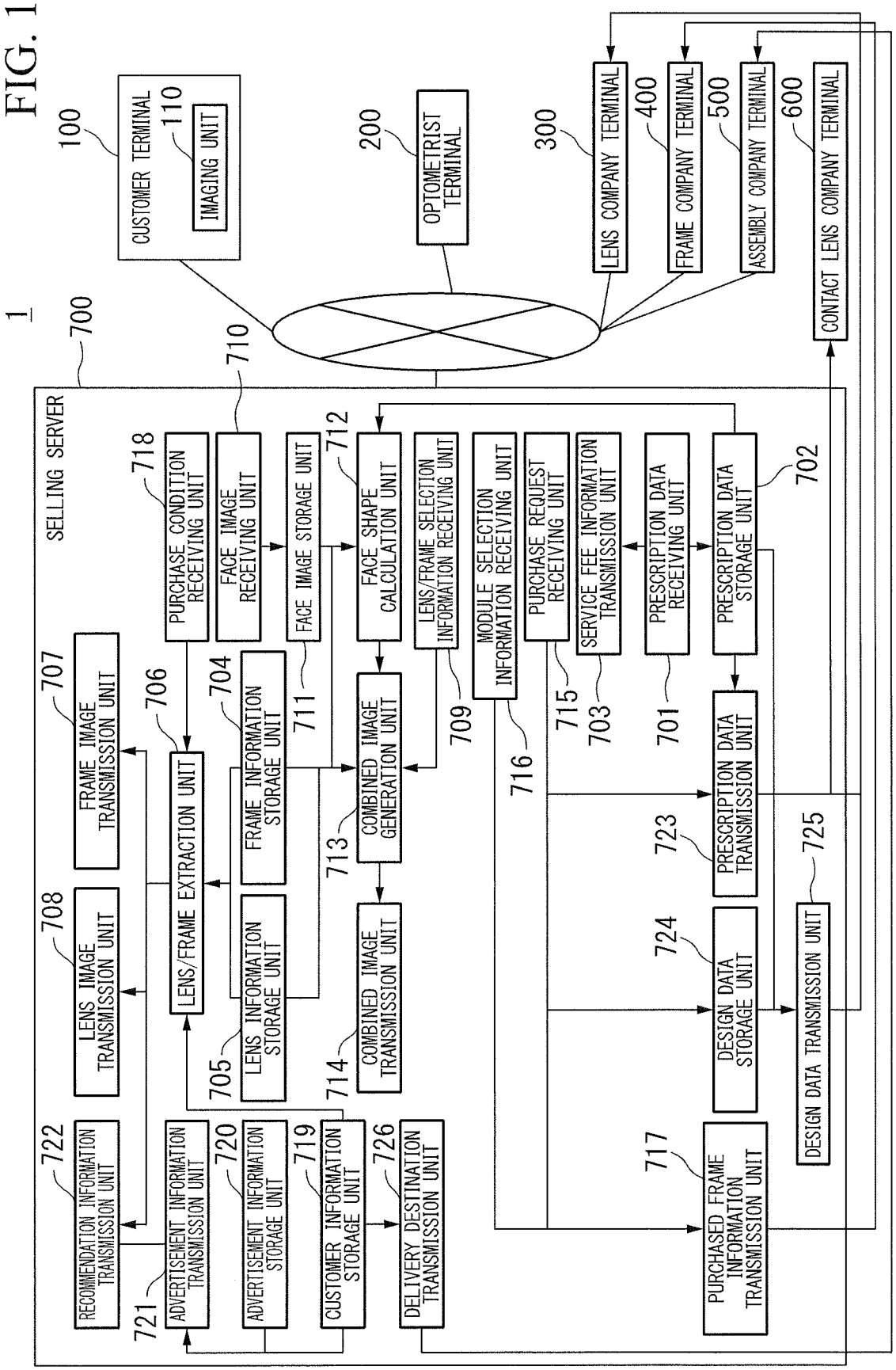
FIG. 1 is a block diagram showing a configuration example of a glasses selling system according to an embodiment of the invention.

FIG. 1 is a block diagram showing the configuration of a glasses selling system 1 of this embodiment. The glasses selling system 1 includes computer devices of a customer terminal 100, an optometrist terminal 200, a lens company terminal 300, a frame company terminal 400, an assembly company terminal 500, a contact lens company terminal 600, and a selling server 700, and these computers are connected together through a communication line. Although in this embodiment, a case where each computer device has a single computer device has been described, each computer device may have a plurality of computer devices. For example, the glasses selling system 1 may include a plurality of customer terminals 100 which are used by a plurality of customers, a plurality of optometrist terminals 200 which are used by a plurality of optometrists, or the like.

The customer terminal 100 is a computer device of a customer (user) who purchases glasses using the glasses selling system 1. As the customer terminal 100, specifically, a PC (Personal Computer), a PDA (Personal Digital Assistant), a mobile phone terminal, or the like may be applied. In this embodiment, a case where a PC is applied as the customer terminal 100 will be described. The customer terminal 100 includes an input unit, such as a keyboard or buttons, which receives information input from the customer, a display unit, such as a display, which displays input information or information transmitted from the selling server 700 or the like, and the like. The customer terminal 100 has a function of an Internet browser which performs Internet communication on the basis of HTTP (HyperText Transfer Protocol) or the like. The customer terminal 100 includes an imaging unit 110. The imaging unit 110 is a camera which captures a face image or the like of the customer. While the imaging unit 110 may be a camera which captures a still image, in this embodiment, a case where the imaging unit 110 is a camera (a web camera) which captures a motion image will be described. The customer terminal 100 is operated by the customer, and the imaging unit 110 is directed so as to image the face of the customer, such that the imaging unit 110 captures the face image of the customer. The customer terminal 100 transmits information input to the input unit, image data of the face image captured by the imaging unit 110, or the like to the selling server 700 through the communication line.

The optometrist terminal 200 is the computer device of the optometrist who performs optometry for a glasses prescription. As the optometrist terminal 200, a similar PC as the customer terminal 100, or the like may be applied. The optometrist is, for example, an ophthalmologist, a clerk who performs optometry of the customer at a glasses shop, or the like. During optometry, for example, a preliminary test, such as a medical interview, a visual acuity test, a cover test, or an effect test, an objected test, such as a corneal curvature test or a refraction test, a subjective test, a wearing test using a test frame, and the like are performed. Prescription data including an inter-pupil distance, myopic power, hyperopic power, astigmatic power, an astigmatic axis angle, prism power, and the like are input to the optometrist terminal 200 as the result of optometry. Prescription data input to the optometrist terminal 200 is transmitted to the selling server 700 for a glasses prescription through the communication line.

As the optometrist terminal 200, a movable radio station, such as a notebook PC, which is connectable to the communication line using wireless communication, may be applied. The optometrist terminal 200 transmits prescription data input by the optometrist to the selling server 700 through a wireless communication line. Alternatively, the optometrist, such as an ophthalmologist, may visit a customer by automobile or the like, and may transmit prescription data from an in-vehicle antenna. While this optometry should be performed by the optometrist with specialized knowledge relating to the glasses and the like, for example, the optometrist can visit an area where there is no glasses shop with the movable optometrist terminal 200 and can perform optometry of a customer who resides in the area, and the optometrist terminal 200 can receive input of prescription data and can transmit prescription data to the selling server 700. Accordingly, it is possible to provide appropriate glasses for a customer who resides in an area where there are no glasses shops.

The lens company terminal 300 is a computer device of a lens company which designs, manufactures, and processes a lens for glasses. As the lens company terminal 300, a similar PC as the customer terminal 100, or the like may be applied. The lens company designs, manufactures, and processes a lens on the basis of prescription data transmitted from the selling server 700 to the lens company terminal 300, or the like. Lens design refers to design of the shape of a lens on the basis of prescription data. Lens processing refers to processing of a lens on the basis of lens design. Lens design and lens processing may be performed by the same company, or may be performed by different companies. The lens company may manufacture and process a lens on the basis of design data of the lens transmitted from the selling server 700 to the lens company terminal 300.

The frame company terminal 400 is a computer device of a frame company which designs, manufactures, and processes a frame for glasses. As the frame company terminal 400, a similar PC as the customer terminal 100, or the like may be applied. The frame company manufactures and processes a frame on the basis of module selection information, prescription data, or the like transmitted from the selling server 700 to the frame company terminal 400.

The assembly company terminal 500 is a computer device of an assembly company which inserts a lens manufactured and processed by the lens company into a frame manufactured and processed by the frame company to assemble the glasses. If a lens and a frame arrive, the assembly company measures the frame shape using a frame tracer. The lens is processed on the basis of the measured frame shape using a lens edger. If the lens is placed in the frame and the glasses are assembled, the assembly company delivers the glasses to the customer. The assembly company delivers the glasses to the customer as a delivery destination on the basis of the delivery destination of the glasses transmitted from the selling server 700 to the assembly company terminal 500. As the assembly company terminal 500, a similar PC as the customer terminal 100, or the like may be applied.

The contact lens company terminal 600 is a computer device of a contact lens company which designs, manufactures, and processes a contact lens based on prescription data. The contact lens company manufactures and processes a contact lens on the basis of prescription data transmitted from the selling server 700 to the selling server 700, information representing the delivery destination of the contact lens to the customer, or the like, and delivers an appropriate contact lens to the customer.

The selling server 700 is a computer device which performs communication with a plurality of computer devices connected thereto through the communication line and controls glasses selling to the customer. The selling server 700 has a function of a web browser, and provides a glasses fitting screen on which the customer virtually wears the glasses. The selling server 700 provides a web service in which a combined image of the face image of the customer and the image of the glasses can be generated in accordance with access from the customer terminal 100 and transmitted to the customer terminal 100, and the customer can virtually wear the glasses and can confirm the wearing state of the glasses. If a request to purchase the glasses virtually fitted to the customer is received from the customer terminal 100, the selling server 700 performs information communication with the lens company terminal 300, the frame company terminal 400, or the like, and delivers the glasses processed for the customer to the customer.

The selling server 700 includes a prescription data receiving unit 701, a prescription data storage unit 702, a service fee information transmission unit 703, a frame information storage unit 704, a lens information storage unit 705, a lens/frame extraction unit 706, a frame image transmission unit 707, a lens image transmission unit 708, a lens/frame selection information receiving unit 709, a face image receiving unit 710, a face image storage unit 711, a face shape calculation unit 712, a combined image generation unit 713, a combined image transmission unit 714, a purchase request receiving unit 715, a module selection information receiving unit 716, a purchased frame information transmission unit 717, a purchase condition receiving unit 718, a customer information storage unit 719, an advertisement information storage unit 720, an advertisement information transmission unit 721, a recommendation information transmission unit 722, a prescription data transmission unit 723, a design data storage unit 724, a design data transmission unit 725, and a delivery destination transmission unit 726.

The prescription data receiving unit 701 receives prescription data as the optometry result on the customer by the optometrist from the optometrist terminal 200.

The prescription data storage unit 702 stores prescription data of the customer transmitted from the optometrist terminal 200 in association with customer identification information (user ID or the like) for identifying the customer. FIG. 2 is a diagram showing a data example of prescription data which is stored in the prescription data storage unit 702.

The service fee information transmission unit 703 transmits predetermined service fee information to the optometrist terminal 200 in accordance with prescription data transmitted from the optometrist terminal 200 to the selling server 700. In this way, as a rebate when the optometrist performs optometry of the customer and inputs prescription data to the optometrist terminal 200 to transmit prescription data to the selling server 700, an administrator of the selling server 700 pays money or the like to the optometrist. Accordingly, an incentive when the optometrist performs optometry of the customer is secured. The payment may be made by cash transfer, electronic money, or the like.

Figure 7:
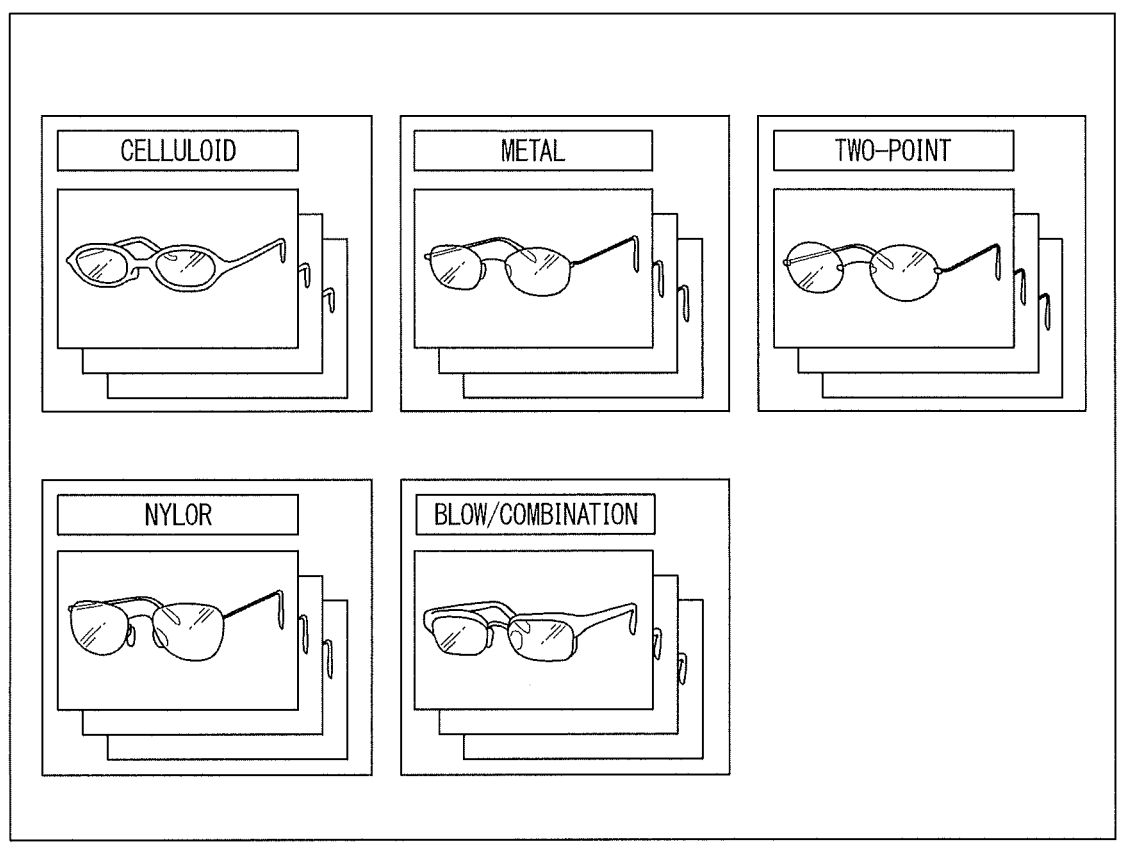
FIG. 7 is a diagram showing an example of a frame material which is stored in a frame information storage unit according to an embodiment of the invention.
Figure 8:
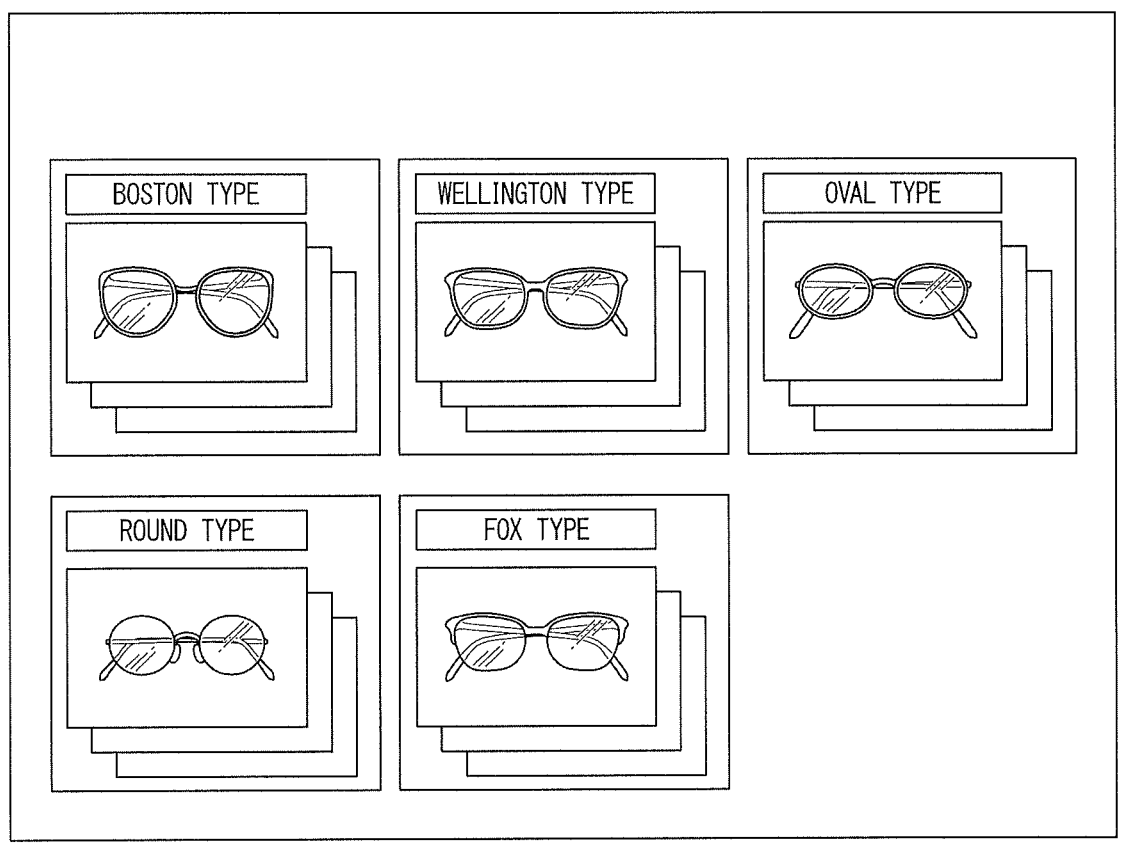
FIG. 8 is a diagram showing an example of a frame shape which is stored in a frame information storage unit according to an embodiment of the invention.

The frame information storage unit 704 stores image data of a frame candidate group of glasses to be sold to the customer. For example, the frame information storage unit 704 stores image data of various types of frames according to the frame's materials, shape, color, price, and the like in association with frame identification information for identifying the frames. FIG. 7 is a diagram showing an example of a frame material which is stored in the frame information storage unit 704. Examples of the frame material include celluloid, metal, two-point (rimless), Nylor (groove excavation), combination (blow, combination), and the like. FIG. 8 is a diagram showing an example of a frame shape which is stored in the frame information storage unit 704. Examples of the frame shape include a Boston type, a Wellington type, an oval type, a round type (Lloyd type), a fox shape, and the like. The frame information storage unit 704 may store images of a plurality of articles for each portion (module), such as a front, a temple, or a bridge, which constitutes a frame. In this case, information, such as materials and fee, may be stored in terms of the modules. The period required until the frame is assembled, or the like may be stored in terms of the combinations of the modules. In this way, a plurality of kinds of image data for the respective modules stored in the frame information storage unit 704 can be transmitted to the customer terminal 100, the selection of a favorite article for each module can be received, and a frame using the selected module can be sold.

The lens information storage unit 705 stores image data of a lens candidate group of glasses to be sold to the customer. For example, the lens information storage unit 705 stores a plurality of kinds of lenses according to the lenses' materials, surface treatment, color, depth of the color, weight, and price, and the like in association with lens identification information for identifying the lenses. The lenses which are stored in the lens information storage unit 705 include colored lenses. Examples of the colored lenses include a lens with low color density which is used in daily life for fashion, anti-glare effect, or the like, a lens with high color depth which is used for protection from light at a place where the sun is strong, and the like.

The lens/frame extraction unit 706 reads image data of a frame to be transmitted to the customer terminal 100 in the frame candidate group stored in the frame information storage unit 704 and image data of a lens to be transmitted to the customer terminal 100 in the lens candidate group stored in the lens information storage unit 705. The lens/frame extraction unit 706 extracts a lens or a frame to be presented to the customer on the basis of, for example, attribute information or purchase history of the customer stored in the customer information storage unit 719 in advance, the purchase conditions received by the purchase condition receiving unit 718 from the customer terminal 100, and the like.

For example, the lens/frame extraction unit 706 reads, from the frame information storage unit 704 or the lens information storage unit 705, a lens or a frame according to the purchase conditions received by the purchase condition receiving unit 718 from the customer terminal 100. The purchase conditions include, for example, the time limit up to the delivery of the glasses, price, and the like. The frame information storage unit 704 or the lens information storage unit 705 stores the period from order placement to processing completion, price, and the like in an associated manner, and the lens/frame extraction unit 706 extracts a lens or a frame satisfying the purchase conditions from the frame information storage unit 704 or the lens information storage unit 705 with reference to the information.

Alternatively, the lens/frame extraction unit 706 may extract a lens or a frame to be recommended to the user in accordance with, for example, the purchase history of the customer stored in the customer information storage unit 719. For example, a category according to the type of frame or lens is stored in the frame information storage unit 704 or the lens information storage unit 705 in advance, and a popular frame or lens (a frame or a lens which is frequently purchased by other customers) may be extracted from among frames or a lenses in the same category as the frame or the lens purchased by the customer. A frame or a lens of the same color or in the same price range as the frame or the lens purchased by the customer may be extracted.

The frame image transmission unit 707 transmits image data of the frame candidate group of the glasses stored in the frame information storage unit 704 and read by the lens/frame extraction unit 706 to the customer terminal 100. When image data for each module is extracted by the lens/frame extraction unit 706, the frame image transmission unit 707 transmits image data for each module to the customer terminal 100.

The lens image transmission unit 708 transmits image data of the lens candidate group stored in the lens information storage unit 705 and read by the lens/frame extraction unit 706 to the customer terminal 100.

The lens/frame selection information receiving unit 709 receives, from the customer terminal 100, identification information for identifying the lens or frame selected by the customer terminal 100 from among image data transmitted from the frame image transmission unit 707 or the lens image transmission unit 708 to the customer terminal 100.

The face image receiving unit 710 receives the face image of the customer transmitted from the customer terminal 100. It is assumed that the face image received by the face image receiving unit 710 is, for example, a motion image. The face image receiving unit 710 receives a motion image in which the direction, expression, or the like of the face of the customer is possible to change with time.

The face image storage unit 711 stores the face image of the customer received by the face image receiving unit 710.

Figure 3:
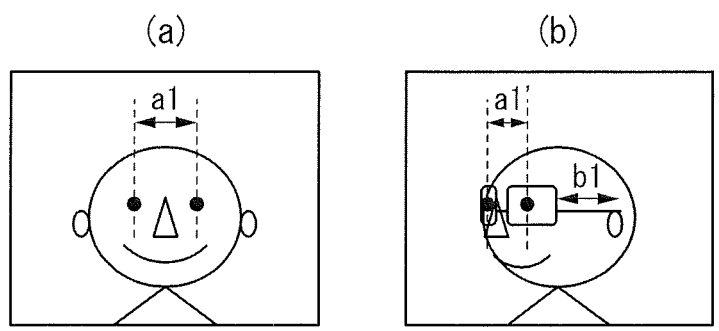
FIG. 3 is a diagram showing an example of a face shape which is calculated in an embodiment of the invention.

The face shape calculation unit 712 calculates face shape information necessary for manufacturing the glasses from the face image stored in the face image storage unit 711 on the basis of the inter-pupil distance of prescription data stored in the prescription data storage unit 702. For example, the face shape calculation unit 712 calculates the positions of the eyes or the positions of the ears through face recognition processing on the image. For example, the distance represented by reference numeral a1 of FIG. 3(a) corresponds to the inter-pupil distance stored in the prescription data storage unit 702. Accordingly, the shape of the face can be calculated on the basis of the length of reference numeral a1 in the image. For example, as shown in FIG. 3(b), when the customer turns his/her face sideways, as represented by reference numeral a1', the inter-pupil distance becomes shorter than the length of a1 in FIG. 3(a). Hence, the glasses frame is combined with the face image, and the length of the temple represented by reference numeral b1 when a person wears the glasses is calculated on the basis of change in the length, using, for example, a ray-tracing technique in the three-dimensional computer graphics. The face shape information includes, for example, pupil height, pad width, pad height, pad tilt angle, front width, front tilt angle, armor height, armor aperture angle, temple length, bending angle, eye-point position, pad interval, pad depth, ear cover bending angle, and the like. In this way, the face shape calculation unit 712 calculates the face shape information necessary for manufacturing the glasses.

Figure 4:
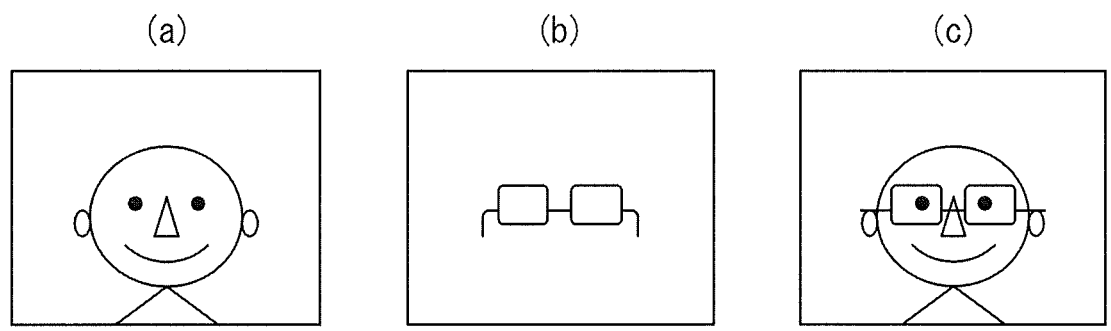
FIG. 4 is a diagram showing an example of a combined image which is generated in an embodiment of the invention.

The combined image generation unit 713 generates a combined image of the frame image selected by the customer, the lens image selected by the customer, and the face image of the customer. For example, the combined image generation unit 713 combines a face image shown in FIG. 4(a) and a frame image shown in FIG. 4(b) using the technique in the three-dimensional computer graphics to generate a combined image shown in FIG. 4(c) in which the frame is worn on the face of a person. The combined image generation unit 713 may superimpose a frame image in front view at a coordinate position set in advance on the screen of a face image to generate a combined image, or may calculate the coordinate positions of the eyes on a face image calculated through face recognition processing and may generate a combined image such that both eyes fall within the front frame of the frame. The combined image generation unit 713 may adjust the position of the frame for the face image in accordance with an operation input to the customer terminal 100. The combined image generation unit 713 generates a high-definition and high-quality image such that the texture of the frame or lens is easily confirmed.

Figure 5:
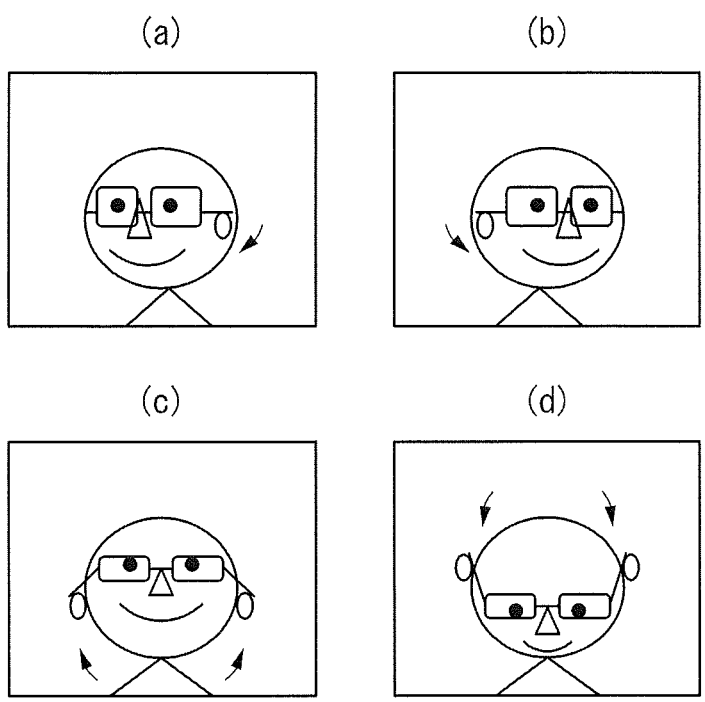
FIG. 5 is a diagram showing an example of a combined image which is generated in an embodiment of the invention.

The combined image generation unit 713 generates a combined image so as to follow the motion of the face image based on a motion image captured by and transmitted from the imaging unit 110 of the customer terminal 100. For example, as shown in FIG. 5(a) or 5(b), when the customer who faces the front turns his/her face sideways, a combined image is generated such that the glasses are at the positions of the eyes in accordance with the direction of the face. Similarly, as shown in FIG. 5(c) or 5(d), when the customer turns his/her face up and down, a combined image is generated such that the glasses are at the positions of the eyes in accordance with the direction of the face. At this time, the combined image generation unit 713 may generate combined images at a fixed time interval, such as one-tenth second, or may generate a combined image when the motion of the face image is detected.

In a case that the combined image generation unit 713 generates a combined image, when a colored lens is selected by the customer terminal 100, a combined image in which color according to the selected colored lens is combined in the lens portion is generated. In this case, for example, how much the landscape look changed in color in connection with the selected lens color and depth may be simulated and displayed on the screen. This simulation compares and displays the landscape viewed with a colorless glasses and the landscape viewed with a colored glasses (parameters of color and depth), and compares and displays the lens portion of the combined image while changing the color. The customer can select the color and depth while confirming the landscape viewed by the customer and the customer's face viewed by other people from the color and the depth. An image generated by the combined image generation unit 713 may be displayed while enlarging a specific part in accordance with an operation input to the customer terminal 100, or may be rotated and displayed. The combined image generation unit 713 generates an image representing the thickness of the lens side surface in a state where the lens is placed in the glasses frame selected by the customer terminal 100. For example, the combined image generation unit 713 may generate an image by calculating the thickness of the lens side surface on the basis of design data of the lens transmitted from the lens company terminal, or may generate an image on the basis of the thickness of the lens side surface stored in the selling server. The combined image generation unit 713 may record the motion image of the generated combined image in accordance with a request from the customer terminal 100 and may reproduce the recorded motion image at an arbitrary point of time. Accordingly, even an image, in which the customer turns his/her face sideways, from among the images of the customer allows the customer to make confirmation.

The combined image transmission unit 714 transmits the combined image generated by the combined image generation unit 713 to the customer terminal 100.

The purchase request receiving unit 715 receives information relating to a frame and a lens purchased by the customer and determined by the customer on the basis of the combined image transmitted from the combined image transmission unit 714 to the customer terminal 100. The purchase request receiving unit 715 receives the frame identification information for identifying the frame purchased by the customer and the lens identification information for identifying the lens from the customer terminal 100. When selling a contact lens, the purchase request receiving unit 715 may receive a request to purchase a contact lens transmitted from the customer terminal 100.

The module selection information receiving unit 716 receives module selection information representing a combination of modules selected by the customer using the customer terminal 100 to purchase in accordance with the frame image for each module transmitted from the frame image transmission unit 707. The module selection information receiving unit 716 receives identification information for each module.

The purchased frame information transmission unit 717 transmits information relating to the frame which the customer selected to purchase to the frame company terminal 400. For example, the purchased frame information transmission unit 717 transmits the frame identification information received by the purchase request receiving unit 715 or the module selection information received by the module selection information receiving unit 716 to the frame company terminal 400.

Figure 9:
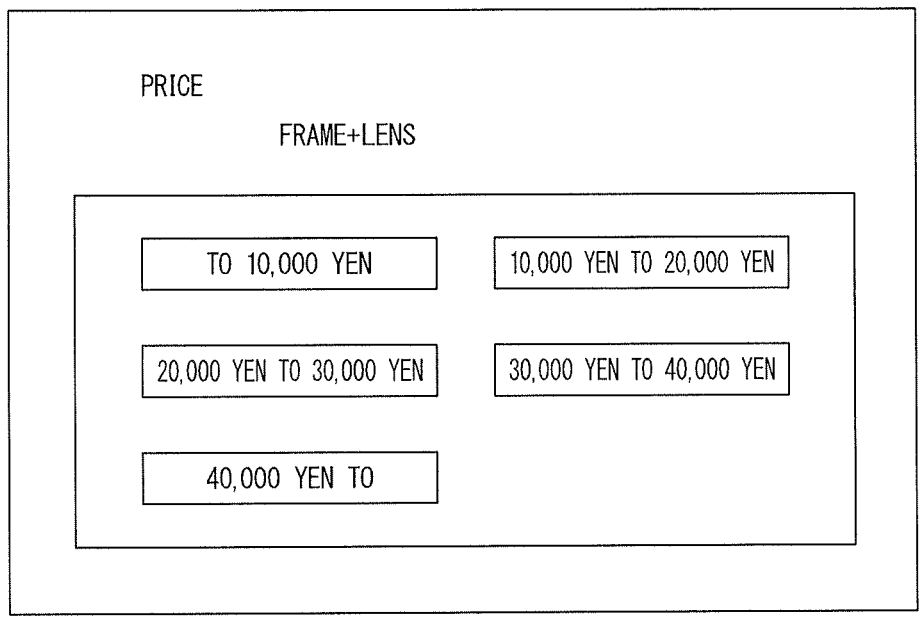
FIG. 9 is a diagram showing an example of a price selection screen which is displayed on a customer terminal according to an embodiment of the invention.

The purchase condition receiving unit 718 receives purchase condition information including at least one of the time limit up to the delivery of the glasses and price from the customer terminal 100. The customer inputs the purchase condition information to the customer terminal 100, and the customer terminal 100 transmits the input purchase condition information to the selling server 700. FIG. 9 is a diagram showing an example of a price selection screen which is displayed on the customer terminal 100. Prices of the glasses, such as, for example, lower than 10,000 yen (to 10,000 yen), 10,000 yen level (10,000 yen to 20,000 yen), 20,000 yen level (20,000 yen to 30,000 yen), 30,000 yen level (30,000 yen to 40,000 yen), equal to or higher than 40,000 yen (40,000 yen to), can be input. As the time limit up to the delivery of the glasses, for example, an arbitrary time limit ranging from the same day (one day) to one month can be input.

The customer information storage unit 719 stores personal data associated with information relating to the customer for customer identification information to identify the customer. Personal data includes attribute information, such as the name, date of birth (birthday), address, sex, mail address, designated date (the date designated by the customer, anniversary, date of birth, or the like) of the customer. Usage registration is received from the customer terminal 100 to the glasses selling system 1 in advance, and the attribute information is input from the customer to the customer terminal 100 at the time of usage registration, and transmitted to and stored in the selling server 700. At this time, the selling server 700 generates customer identification information to identify the customer, and the customer identification information is stored in the customer information storage unit 719 in association with information transmitted from the customer terminal 100.

Personal data includes information representing the delivery destination of the glasses manufactured and processed in accordance with a purchase request from the customer. The delivery destination may be the address of the customer. Personal data also includes a purchase history representing the purchase request transmitted from the customer terminal 100. The purchase history includes, for example, the date on which the customer purchases the glasses, identification information of the lens or the frame, prescription data, and the like. A password according to the customer identification information may be registered, and the selling server 700 may perform a process to log in to the selling server 700 with the customer identification information (user ID or the like) and the password. Personal data stored in the customer information storage unit 719 may store credit card information or the like which is used when the customer pays for the purchased glasses.

The advertisement information storage unit 720 stores advertisement information relating to the frame stored in the frame information storage unit 704, the lens stored in the lens information storage unit 705, or the like. The advertisement information is, for example, character information, image information, or the like. The advertisement information may include, for example, information relating to a discount of glasses selling.

The advertisement information transmission unit 721 reads the advertisement information stored in the advertisement information storage unit 720 and transmits the advertisement information to the customer terminal 100. For example, the advertisement information transmission unit 721 reads information representing the designated date (for example, the date of birth) in a plurality of kinds of customer information stored in the customer information storage unit 719, and compares the read designated date (month and day) with the current month and day obtained using an internal timer function. If it is determined that the read date of birth matches the current month and day, the advertisement information transmission unit 721 transmits the advertisement information stored in the advertisement information storage unit 720 to the customer terminal 100. When it is determined that the date before a predetermined period from the designated date (for example, the date before one month from the date of birth) matches the current month and day, the advertisement information transmission unit 721 may transmit the advertisement information stored in the advertisement information storage unit 720 to the customer terminal 100.

The recommendation information transmission unit 722 transmits the information of the frame or the lens extracted by the lens/frame extraction unit 706 in accordance with the purchase history in personal data stored in the customer information storage unit 719 to the customer terminal 100.

The prescription data transmission unit 723 transmits prescription data of the customer stored in the prescription data storage unit 702 to the lens company terminal 300 of the lens company which manufactures the lens purchased by the customer or the frame company terminal 400 of the frame company which manufactures the frame purchased by the customer. When a request to purchase a contact lens is transmitted from the customer terminal 100, the prescription data transmission unit 723 transmits prescription data of the customer stored in the prescription data storage unit 702 to the contact lens company terminal 600.

The design data storage unit 724 stores design data of the lens according to prescription data in advance. Design data is, for example, information in which the shape of the lens surface according to prescription data is represented by the coordinates in the three-dimensional space. The design data storage unit 724 stores, for example, design data for each of materials, coating, coloring or design, such as spherical design or aspheric design, in accordance with myopic power, hyperopic power, astigmatic power, or the like.

The design data transmission unit 725 reads design data of the lens according to prescription data of the customer in accordance with information relating to the lens received by the purchase condition receiving unit 718, and transmits design data to the lens company terminal 300.

The delivery destination transmission unit 726 transmits the delivery destination corresponding to the customer to the assembly company terminal 500 of the assembly company which assembles the frames and the lens purchased by the customer. The delivery destination transmission unit 726 reads the delivery destination corresponding to the customer who purchases the glasses from personal data stored in the customer information storage unit 719, and transmits the delivery destination to the assembly company terminal 500. The assembly company delivers the assembled glasses with the delivery destination transmitted from the delivery destination transmission unit 726 as a destination.

Figure 6:
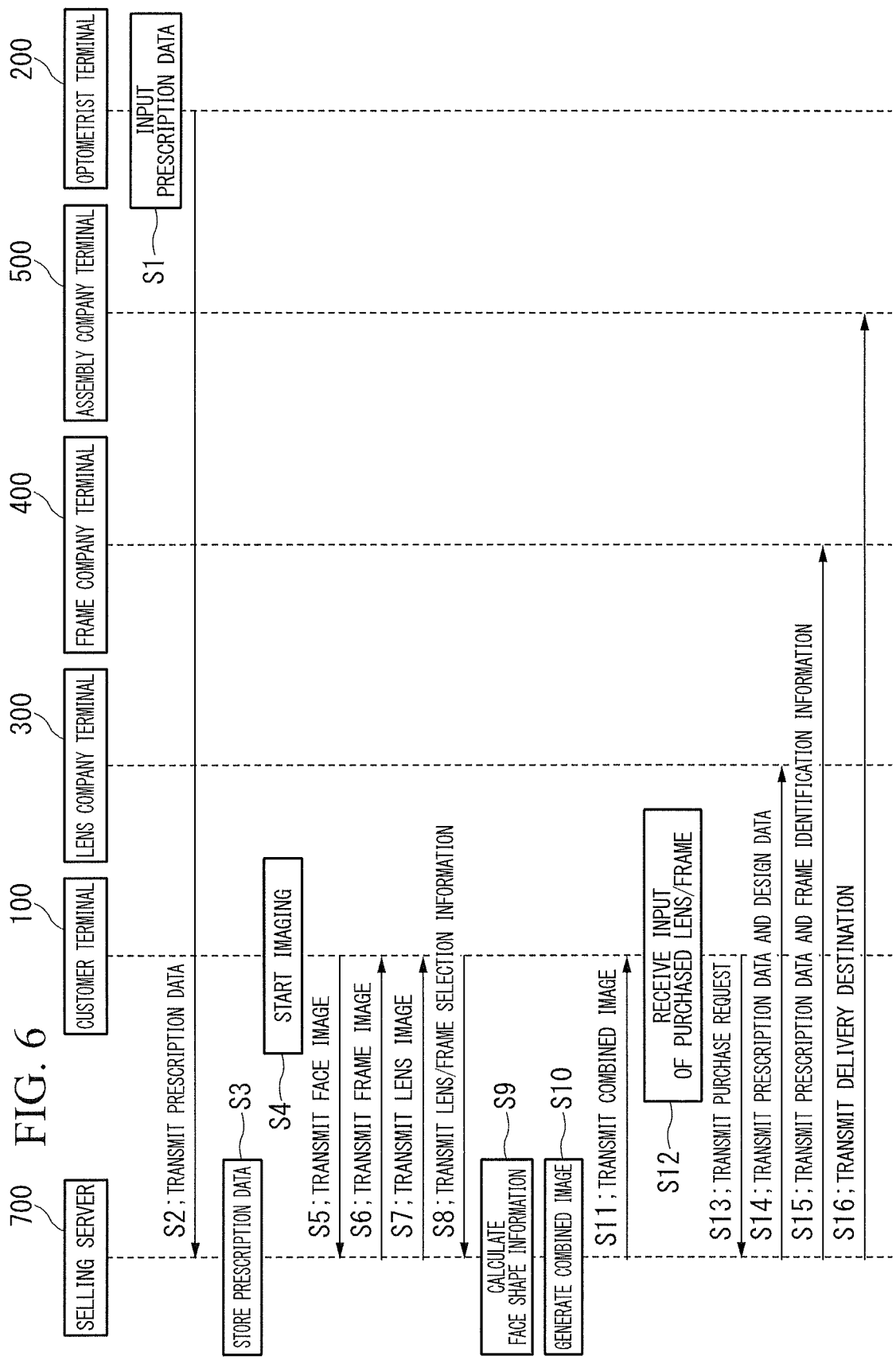
FIG. 6 is a sequence diagram showing an operation example of a glasses selling system according to an embodiment of the invention.

Next, an operation example of the glasses selling system 1 of this embodiment will be described. FIG. 6 is a sequence diagram showing an operation example where glasses are sold by the glasses selling system 1 using information communication through the communication line.

For example, the customer terminal 100 accesses the selling server 700 in advance in accordance with an operation input from the customer, and transmits personal data, such as the name or the address, to the selling server 700. The selling server 700 generates customer identification information (user ID or the like) for identifying the customer, and stores the customer identification information in the customer information storage unit 719 in association with personal data transmitted from the customer terminal 100. The selling server 700 transmits the generated customer identification information to the customer terminal 100.

After optometry of the customer is performed, the optometrist inputs prescription data based on the optometry result to the optometrist terminal 200. The optometrist terminal 200 receives prescription data input by the optometrist (Step S1). At this time, for example, the optometrist hears from the customer identification information given to the customer in advance, and inputs the customer identification information to the optometrist terminal 200. The optometrist terminal 200 transmits input prescription data to the selling server 700 in association with the customer identification information (Step S2). If prescription data and the customer identification information transmitted from the optometrist terminal 200 are received, the prescription data receiving unit 701 of the selling server 700 stores prescription data and the customer identification information in the prescription data storage unit 702 (Step S3).

The customer terminal 100 accesses the selling server 700 in accordance with an operation input from the customer, and for example, transmits the user ID and the password given in advance to log in to the web service which is provided by the selling server 700. The selling server 700 transmits the glasses fitting screen to the customer terminal 100. The imaging unit 110 of the customer terminal 100 starts to capture the face image of the customer (Step S4). The customer terminal 100 transmits the face image captured by the imaging unit 110 to the selling server 700 (Step S5). An image which is captured by the imaging unit 110 and transmitted to the selling server 700 is, for example, a motion image, and hereinafter, the customer terminal 100 continues to transmit the face image of the customer captured by the imaging unit 110.

The lens/frame extraction unit 706 of the selling server 700 extracts a frame image for each type of frame shape from the frame candidate group stored in the frame information storage unit 704 and transmits the frame image to the customer terminal 100 (Step S6). The lens/frame extraction unit 706 extracts the lens image for each type of lens image for each type of lens material from the lens candidate group stored in the lens information storage unit 705 and transmits the lens image to the customer terminal 100 (Step S7). The customer terminal 100 displays a plurality of frame images and lens images transmitted from the selling server 700 on the display unit. For example, the customer terminal 100 may display a plurality of frame images or lens images on one screen, or may sequentially display one frame image or lens image on one screen. The customer selects a frame and a lens for the customer's preference from the frame images and the lens images displayed on the display unit of the customer terminal 100. If the input of information representing the frame and the lens selected by the customer is received, the customer terminal 100 transmits frame identification information for identifying the selected frame and lens identification information for identifying the selected lens to the selling server 700 (Step S8). The lens/frame selection information receiving unit 709 of the selling server 700 receives the lens identification information and the frame identification information transmitted from the customer terminal 100.

The face image receiving unit 710 of the selling server 700 receives the face image which starts to be transmitted in Step S5, and stores the face image in the face image storage unit 711. The face shape calculation unit 712 calculates face shape information on the basis of the face image stored in the face image storage unit 711 (Step S9). The combined image generation unit 713 reads the lens according to the lens identification information received by the lens/frame selection information receiving unit 709 from the lens information storage unit 705. The combined image generation unit 713 reads the frame according to the frame identification information received by the lens/frame selection information receiving unit 709 from the frame information storage unit 704.

The combined image generation unit 713 generates a combined image on the basis of the face image stored in the face image storage unit 711, the face shape information calculated by the face shape calculation unit 712, the frame image read from the frame information storage unit 704, and the lens image read from the lens information storage unit 705 (Step S10). The combined image transmission unit 714 of the selling server 700 transmits the combined image generated by the combined image generation unit 713 to the customer terminal 100 (Step S11). If the combined image transmitted from the selling server 700 is received, the customer terminal 100 displays the combined image on the display unit. The customer views the combined image displayed on the display unit to confirm the wearing state when the customer fits the glasses on. In this case, the combined image is generated by the selling server 700 in real time on the basis of the face image captured by the imaging unit 110 and transmitted to the selling server 700, and transmitted to and displayed on the customer terminal 100. When the customer wants to view a combined image in which another lens and frame are fitted, the customer reselects a frame and a lens, and inputs the frame and the lens to the customer terminal 100. The customer terminal 100 transmits identification information of the selected frame and identification information of the lens to the selling server 700, and the processing of Steps S8 to S11 is repeated, such that the customer can view combined images in which a plurality of frames and images are fitted.

If the customer selects a frame and a lens which the customer wants to purchase, the customer inputs information representing a purchase intention to the customer terminal 100. If the input of the frame and the lens which are input from the customer is received (Step S12), the customer terminal 100 transmits a request to purchase the input frame and lens to the selling server 700 (Step S13). If the purchase request receiving unit 715 of the selling server 700 receives the purchase request transmitted from the customer terminal 100, the prescription data transmission unit 723 reads prescription data stored in the prescription data storage unit 702, and transmits prescription data to the lens company terminal 300. The design data transmission unit 725 reads design data according to prescription data stored in the prescription data storage unit 702 from the design data storage unit 724, and transmits the design data to the lens company terminal 300 (Step S14). Design data includes the lens identification information selected by the customer terminal 100. The lens company may create design data of the lens on the basis of prescription data or the like transmitted from the selling server 700 to the lens company terminal 300. The purchased frame information transmission unit 717 transmits the frame identification information and prescription data included in the purchase request received by the purchase request receiving unit 715 to the frame company terminal 400 (Step S15). The selling server 700 transmits the delivery destination of the glasses to the frame company terminal 400 (Step S16).

If the lens is manufactured and processed by the lens company on the basis of prescription data and design data received by the lens company terminal 300, the processed lens is delivered to the assembly company terminal 500. If the frame is manufactured and processed by the frame company on the basis of prescription data and the frame identification information received by the frame company terminal 400, the processed frame is delivered to the assembly company. The frame company may deliver the stock of the frame corresponding to the frame identification information received by the frame company terminal 400 to the assembly company. If the lens delivered from the lens company and the frame delivered from the frame company are processed and assembled, in Step S16, the assembly company delivers the assembled glasses to the delivery destination of the glasses received by the assembly company terminal 500.

As described above, according to this embodiment, all the steps necessary for purchasing the glasses including the input of prescription data by the optometrist, the selection of the frame and the lens by the customer, the processing of the lens by the lens company according to prescription data based on the optometry result, and the delivery of the assembled glasses to the customer can be performed through the network. Accordingly, the customer can more easily purchase appropriate glasses according to the optometry result of the customer through the network without visiting the glasses shop. For this reason, for example, even when the customer resides in an area where there is no glasses shop, the customer can purchase the glasses, and the glasses seller can sell the glasses. Since an actual glasses shop is not required, costs of actual shop operation for glasses selling can be reduced, and efficient distribution can be made. In this way, according to this embodiment, it becomes possible to easily sell appropriate glasses to customers in a wider area with lower cost.

Although in this embodiment, a case where the optometrist terminal 200 is a movable radio station has been described, for example, the optometrist may visit an area where there is no glasses shop, may perform optometry of a customer, and may store prescription data in a portable storage medium, such as a USB (Universal Serial Bus) memory or a CD (compact disc), through the optometrist terminal 200, and the selling server 700 or the customer terminal 100 may read prescription data from the portable medium.

Although in this embodiment, the selling server 700 has a function of combining the face image, the frame image, and the lens image to generate the combined image and transmitting the combined image to the customer terminal 100, the function of generating the combined image may be provided in the customer terminal 100. In this case, for example, an animation program which can execute a script may be transmitted from the selling server 700 to the customer terminal 100, and the customer terminal 100 may perform processing for generating the combined image on the basis of the downloaded program.

Although in this embodiment, the combined image in which the lens image, the frame image, and the face image are combined is generated, a combined image in which only the lens image and the frame image are combined may be generated and transmitted to the customer terminal 100. A combined image in which only the frame image and the face image are combined may be generated and transmitted to the customer terminal 100.

The customer information storage unit 719 may store a point or the like according to the purchase history or the like of each customer, and a discount system using the point may be introduced.

When a new article is stored in the frame information storage unit 704 or the lens information storage unit 705, latest information may be transmitted to the customer terminal 100 by mail or the like.

Figure 10:
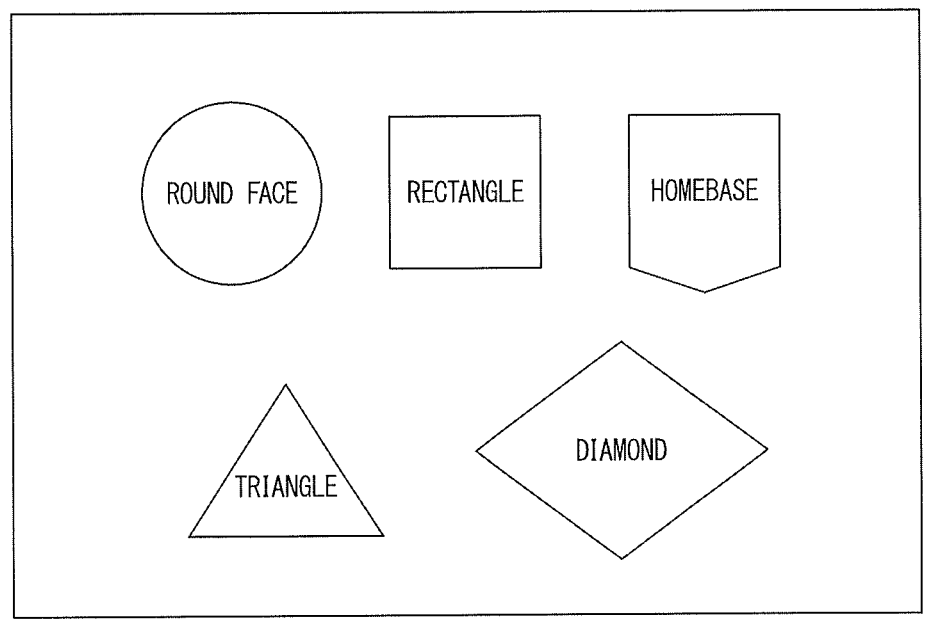
FIG. 10 is a diagram showing an example of a face shape selection screen which is displayed on a customer terminal according to an embodiment of the invention.

The glasses which look good in accordance with the shape of the face in the face image may be recommended on the basis of statistics or information set in advance. FIG. 10 is a diagram showing an example of a face shape selection screen which is displayed on the customer terminal 100. As the face shape, for example, a circle, a triangle, a rectangle, a diamond, a home base, or the like can be input.

The administrator of the glasses selling system 1 may cooperate with the ophthalmologist or the like, and the ophthalmologist may introduce the web service provided by the selling server 700.

In order to determine the performance of an anti-reflection film on the lens, the reflection states of different kinds of lenses may be displayed as images and transmitted to the customer terminal 100, for customer confirmation. For example, how reflection by the lens changes may be simulated in connection with the type of selected lens and displayed on the screen. The customer can select the lens taking into consideration the performance of the anti-reflection film while confirming the reflected color of the lens, the landscape viewed by the customer, the customer's face viewed by other people, and the like from the type of lens.

In order to prevent leakage of individual information, the face image transmitted from the customer terminal 100 to the selling server 700 may be deleted from the storage unit in the selling server 700 when disconnected from the customer terminal 100.

A frame image of an original frame may be created using a drafting tool or the like, and the created frame image may be transmitted to the frame company terminal 400 for manufacturing and processing.

Although in this embodiment, an example where the lens company and the assembly company are different companies has been described, the lens company may perform the steps including edging or V-shape machining on the basis of frame shape measurement data. For example, the frame company may measure the frame shape using a frame tracer, and may transmit information necessary for lens processing to the lens company. The lens company may process the lens using a lens edger on the basis of information transmitted from the frame company. In this case, the assembly company does not process the lens and places the lens in the frame.

The lens company, the frame company, the assembly company, and the contact lens company may be different companies, and two or more of these companies may be the same company.

The administrator of the selling server may be different from the lens company, the frame company, the assembly company, and the contact lens company, or may be the same as any thereof.

The fitting adjustment of the assembled glasses on the ears or the nose of the customer may be performed with the application of a frame which can be adjusted by the customer.

An article other than the glasses may be recommended using information representing the lifestyle from personal data stored in the customer information storage unit 719. For example, information relating to automobiles may be provided to a customer who is fond of automobiles.

A person to whom the customer wants to give a present may be registered in the selling server 700, and a present may be given through the selling server 700.

Although in this embodiment, the lens and the frame to be purchased are selected by the customer on the basis of the combined image, the lens and the frame to be purchased may be selected on the basis of the lens image and the frame image without generating the combined image.

Although in this embodiment, the customer acquires the customer identification information in advance before optometry, the customer identification information may be acquired at the time of optometry. For example, the optometrist terminal 200 may access the selling server 700 in accordance with an operation input from the optometrist, and may acquire customer identification information (user ID or the like) generated by the selling server 700. In this case, the customer may hear the customer identification information acquired by the optometrist terminal 200 from the optometrist.

Design data of the lens may include information representing which of a plurality of semi-materials is used, in addition to the surface shape for processing the semi-material (semi-finished article). If necessary, design data of the lens may include lens shape information, such as the central thickness of the lens, the edge thickness, and the outer diameter, or lens power information for a test of lens refractive power using a lens power measurement device or the like as data for quality confirmation of the processed lens.

Design data of the lens may include surface shape data of the front surface from among the two surfaces of the lens, may include surface shape data of the rear surface, or may include surface shape data of the front and the rear surfaces. Surface shape data may be constituted by a point group (the set of the values of the spatial coordinates (x coordinate, y coordinate, z coordinate) at respective points on the processing surface of the semi-material), may be data obtained by surface-interpolating surface shape data constituted by a point group, or may be data obtained by converting surface-interpolated data to an NC processing program.

The type of processed lens is not limited, and the foregoing embodiment may be applied to a fixed focal lens, a progressive power lens, a progressive lens for middle/near vision, a progressive lens for near/near vision, and the like.

A program for realizing the function of the processing unit according to the invention may be recorded in a computer-readable recording medium, the program recorded in the recording medium may be read into and executed on a computer system to perform glasses selling. It is assumed that the term "computer system" used herein includes an OS or hardware, such as peripherals. It is also assumed that the term "computer system" includes a WWW system which includes a homepage provision environment (or a display environment). The term "computer-readable recording medium" refers to a portable medium, such as a flexible disk, a magneto-optical disk, a ROM, or a CD-ROM, or a storage device, such as a hard disk embedded in the computer system. It is also assumed that the term "computer-readable recording medium" includes a medium which holds a program for a given time, such as a volatile memory (RAM) in the computer system which becomes a server or a client when a program is transmitted through a network, such as Internet, or a communication line, such as a telephone line.

The program may be transmitted from the computer system, which stores the program in the storage device or the like, to other computer systems through a transmission medium or through transmission waves in the transmission medium. The term "transmission medium" which transmits the program refers to a medium which has a function of transmitting information, for example, a network (communication network), such as Internet, or a communication line, such as a telephone line. The program may be a program which can realize part of the above-described functions. The program may be a so-called differential file (differential program) which can realize the above-described functions by a combination with a program already recorded in the computer system.

As described above, the selling server stores prescription data of a customer transmitted from the optometrist terminal of the optometrist performing optometry for a glasses prescription through the communication line in association with customer identification information, transmits image data of a frame candidate group of the glasses to the customer terminal, transmits image data of a lens candidate group of the glasses to the customer terminal, generates a combined image of a frame image selected by the customer, a lens image selected by the customer, and a face image of the customer, receives information relating to a frame and a lens purchased by the customer and determined on the basis of the combined image, and transmits prescription data of the customer to the lens company terminal of the lens company which processes the lens purchased by the customer. For this reason, it becomes possible to provide a glasses selling system which more easily sells more appropriate glasses to a purchaser in accordance with the optometry result of the purchaser.

What is claimed is:

1. A glasses selling system comprising:
a selling server which is connected to a customer terminal of a customer who purchases glasses through a communication line,
wherein the selling server is connected to an optometrist terminal of an optometrist who performs optometry for a glasses prescription through the communication line, and
the selling server includes
a prescription data storage unit which stores prescription data of the customer transmitted from the optometrist terminal in association with customer identification information for identifying the customer,
a frame image transmission unit which transmits image data of a frame candidate group of the glasses to the customer terminal,
a lens image transmission unit which transmits image data of a lens candidate group of the glasses to the customer terminal,
a recommendation information transmission unit which transmits information of glasses representing a frame and a lens recommended for the customer in accordance with a shape of a face of the customer and information representing a lifestyle of the customer,
a purchase request receiving unit which receives information relating to a frame and a lens purchased by the customer, and
a prescription data transmission unit which transmits the prescription data of the customer to a lens company terminal of a lens company manufacturing the lens purchased by the customer,
wherein the selling server or the optometrist terminal includes a combined image generation unit which generates a combined image of a frame image which is an image of the recommended frame, a lens image which is an image of the recommended lens, and a face image of the customer.

2. The glasses selling system according to claim 1,
wherein the prescription data includes information of an inter-pupil distance, and the glasses selling system includes a face shape information calculation unit which calculates face shape information of the customer from the face image on the basis of the inter-pupil distance.

3. The glasses selling system according to claim 1, wherein the optometrist terminal is a movable radio station, and transmits the prescription data to the selling server using wireless communication.

4. The glasses selling system according to claim 1, wherein the customer terminal includes an imaging unit which captures the face image of the customer, and the combined image generation unit generates the combined image so as to follow a motion of the face image captured by the imaging unit.

5. The glasses selling system according to claim 1, wherein the selling server includes a frame information storage unit which stores image data of each of a plurality of modules of the frame, and the frame image transmission unit transmits image data of each of the modules to the customer terminal.

6. The glasses selling system according to claim 5, wherein the selling server includes
a module selection information receiving unit which receives module selection information relating to a combination of the modules selected by the customer, and
a module selection information transmission unit which transmits the module selection information to a frame company terminal of a frame company manufacturing the frame purchased by the customer.

7. The glasses selling system according to claim 1, wherein the selling server includes
a purchase condition receiving unit which receives purchase condition information including a time limit up to a delivery of the glasses or price, and
a lens/frame extraction unit which extracts a frame or a lens satisfying the purchase condition.

8. The glasses selling system according to claim 1, wherein the selling server includes
a customer information storage unit which stores personal data including information representing a designated date of the customer, and
an advertisement information transmission unit which transmits predetermined advertisement information to the customer terminal of the customer corresponding to the designated date on the designated date or before the designated date.

9. The glasses selling system according to claim 1, wherein the selling server includes
a service fee information transmission unit which transmits predetermined service fee information to the optometrist terminal in accordance with the prescription data transmitted from the optometrist terminal.

10. The glasses selling system according to claim 1, wherein the selling server includes
a design data storage unit which stores design data of the lens based on the prescription data in advance, and
a design data transmission unit which transmits design data of the lens based on prescription data of the customer to the lens company terminal in accordance with information relating to the lens received by the purchase request receiving unit.

11. The glasses selling system according to claim 1, wherein the combined image generation unit generates the combined image in which a colored lens selected by the customer terminal is combined.

12. The glasses selling system according to claim 1, wherein the combined image generation unit generates an image representing the thickness of a lens side surface in a state where a lens is fitted into a glasses frame selected by the customer terminal.

13. The glasses selling system according to claim 1, wherein the prescription data includes at least one information of myopic power, hyperopic power, astigmatic power, an astigmatic axis angle, and an inter-pupil distance.

14. The glasses selling system according to claim 1, wherein the selling server includes
a customer information storage unit which stores personal data including information representing a delivery destination of the glasses to the customer, and
a delivery destination transmission unit which transmits the delivery destination corresponding to the customer to an assembly company terminal of an assembly company performing processing for fitting the frame and the lens purchased by the customer.

* * * * *